(12) United States Patent
Nozato et al.

(10) Patent No.: US 9,107,619 B2
(45) Date of Patent: Aug. 18, 2015

(54) OPTICAL-IMAGE PICKUP APPARATUS AND METHOD FOR CONTROLLING THE SAME

(75) Inventors: Koji Nozato, Yokohama (JP); Kazuhide Miyata, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 27 days.

(21) Appl. No.: 13/509,682

(22) PCT Filed: Nov. 2, 2010

(86) PCT No.: PCT/JP2010/006473
§ 371 (c)(1),
(2), (4) Date: May 14, 2012

(87) PCT Pub. No.: WO2011/061896
PCT Pub. Date: May 26, 2011

(65) Prior Publication Data
US 2012/0242872 A1    Sep. 27, 2012

(30) Foreign Application Priority Data

Nov. 17, 2009 (JP) ................. 2009-262387
Sep. 17, 2010 (JP) ................. 2010-209319

(51) Int. Cl.
| | | |
|---|---|---|
| H04N 5/228 | (2006.01) | |
| G21K 7/00 | (2006.01) | |
| A61B 3/12 | (2006.01) | |
| A61B 3/10 | (2006.01) | |
| A61B 3/14 | (2006.01) | |

(52) U.S. Cl.
CPC ............. *A61B 3/1225* (2013.01); *A61B 3/1015* (2013.01); *A61B 3/14* (2013.01)

(58) Field of Classification Search
CPC ...................................................... H04N 5/3675
USPC ................................................... 348/241, 335
See application file for complete search history.

(56) References Cited

U.S. PATENT DOCUMENTS

| | | | |
|---|---|---|---|
| 2002/0016629 A1* | 2/2002 | Sandstedt et al. | 623/6.11 |
| 2003/0197777 A1* | 10/2003 | Miura | 347/235 |
| 2006/0256226 A1* | 11/2006 | Alon et al. | 348/335 |
| 2007/0133372 A1* | 6/2007 | Hirai | 369/112.01 |

(Continued)

FOREIGN PATENT DOCUMENTS

| | | |
|---|---|---|
| EP | 1938745 A1 | 7/2008 |
| GB | 2429522 A | 2/2007 |

(Continued)

OTHER PUBLICATIONS

Y. Zhang et al, "High-speed volumetric imaging of cone photoreceptors with adaptive optics spectral-domain optical coherence tomography", Optics Express, vol. 14, Nos. 10 and 15, May 2006.

*Primary Examiner* — Joel Fosselman
(74) *Attorney, Agent, or Firm* — Canon U.S.A., Inc. IP Division

(57) ABSTRACT

The present invention relates to an optical-image pickup apparatus including a setting unit configured to set the effective region or the resolution of a correction unit configured to correct the aberration of a subject; an aberration measuring unit configured to measure an aberration generated at the subject; and a control unit configured to control the correction unit on the basis of the measured aberration and the set effective region or the measured aberration and the set resolution.

22 Claims, 10 Drawing Sheets

(56) References Cited

U.S. PATENT DOCUMENTS

| | | |
|---|---|---|
| 2007/0158568 A1* | 7/2007 | Nakamura et al. ............ 250/311 |
| 2007/0177026 A1* | 8/2007 | Sasaki ........................ 348/222.1 |
| 2008/0225230 A1 | 9/2008 | Saito |
| 2008/0283750 A1* | 11/2008 | Nakazawa et al. ............ 250/311 |

FOREIGN PATENT DOCUMENTS

| | | | |
|---|---|---|---|
| JP | 2001-000395 A | | 1/2001 |
| JP | 2006034744 | * | 7/2004 |
| WO | 03/020167 A2 | | 3/2003 |

* cited by examiner

OPTICAL-IMAGE PICKUP APPARATUS AND METHOD FOR CONTROLLING THE SAME

TECHNICAL FIELD

The present invention rel tes to an optical image pickup apparatus equipped with an adaptive optic system, as well as a method for controlling the same. In particular, the present invention relates to an optical image pickup apparatus having the function of measuring the aberration of a subject eye and correcting the aberration and capable of image acquisition with a plurality of resolutions, as well as a method for the same.

BACKGROUND ART

In recent years, scanning laser ophthalmoscopes (SLOs) that irradiate the fundus with laser light in two dimensions and receive reflected light therefrom and imaging apparatuses that utilize the interference of low coherence light have been developed as ophthalmic image pickup apparatuses. The imaging apparatuses utilizing the interference of low coherence light are called optical coherence tomography (OCT) systems, which are in particular used to acquire a tomogram of the fundus or the vicinity thereof. Various kinds of OCT have been developed, such as time domain OCT (TD-OCT) and spectral domain OCT (SD-OCT).

In particular, the resolution of such ophthalmic image pickup apparatuses has recently been improved by, for example, achieving high NA of irradiation laser light. However, when an image of the fundus is to be acquired, the image must be acquired through optical tissues including the cornea and the crystalline lens. As the resolution increases, the aberrations of the cornea and the crystalline lens have come to significantly affect the quality of acquired images. Thus, studies of AO-SLO and AO-OCT in which adaptive optics (AO) that is a correction optical system that measures the aberration of the eye and corrects the aberration is incorporated in their optical system have been pursued. An example of AO-OCT is shown in Y. Zhang et al, Optics Express, Vol. 14, Nos. 10 and 15, May 2006. The AO-SLO and AO-OCT generally measure the wavefront of the eye using a Shack-Hartmann wavefront sensor system. The Shack-Hartmann wavefront sensor system measures the wavefront by introducing measurement light into the eye and receiving its reflected light with a CCD camera through a microlens array. A deformable mirror or a spatial-phase modulator is driven to correct the measured wavefront, and an image of the fundus is acquired therethrough, thus allowing AO-SLO and AO-OCT to acquire a high-resolution image.

In general, achieving high NA for irradiation laser light to increase the resolution increases the amount of aberration due to the optical tissues, such as the cornea and the crystalline lens, and forms the aberration into a complicated shape. This aberration is to be corrected by AO; however, to correct a large amount of aberration or an aberration of complicated shape, it is necessary to measure the aberration at high resolution and to drive a wavefront correction device at high resolution. However, it is impossible to correct an aberration beyond the correction capacity of the wavefront correction device. Furthermore, to measure an aberration at high resolution and drive the correction device at high resolution, a large number of calculations are needed, thus posing the significant problem of an increase in calculating time. In particular, since the aberration of the eye should be repeatedly corrected at high speed because the state of tear and the state of visibility control changes constantly, an increase in processing speed is very important.

CITATION LIST

Non Patent Literature

NPL 1: Y. Zhang et al, Optics Express, Vol. 14, Nos. 10 and 15, May 2006

SUMMARY OF INVENTION

In consideration of the above problems, the present invention provides an optical-image pickup apparatus equipped with an adaptive optic system capable of operating a correction device at a suitable effective region or resolution depending on the image acquisition resolution, as well as a method for the same.

A method for controlling an optical-image pickup apparatus according to a first aspect of the present invention is a method for controlling an optical-image pickup apparatus configured to radiate measurement light onto a subject, to correct an aberration generated at the subject with a correction unit, and to acquire an optical image of the subject. The method includes a setting step of setting the effective region or the resolution of the correction unit; a measuring step of measuring an aberration generated at the subject; a calculating step of calculating the amount of aberration of the correction unit on the basis of the measured aberration and the set effective region or the measured aberration and the set resolution; and a control step of controlling the correction unit on the basis of the calculated correction amount.

An optical-image pickup apparatus according to a second aspect of the present invention is an optical-image pickup apparatus configured to radiate measurement light onto a subject, to correct an aberration generated at the subject with a correction unit, and to acquire an optical image of the subject. The apparatus includes a setting unit configured to set the effective region or the resolution of the correction unit; an aberration measuring unit configured to measure an aberration generated at the subject; and a control unit configured to control the correction unit on the basis of the measured aberration and the set effective region or the measured aberration and the set resolution.

According to the above aspects of the present invention, the correction device can be operated at a suitable effective region or resolution depending on the correction state. Furthermore, according to the above aspects of the present invention, the correction device can be operated at a suitable effective region or resolution depending on the image acquisition resolution.

Further features of the present invention will become apparent from the following description of exemplary embodiments with reference to the attached drawings.

DESCRIPTION OF EMBODIMENTS

Embodiments for achieving the present invention will be described hereinbelow.

However, the present invention is not limited by the configurations of the embodiments below.
First Embodiment In a first embodiment, a configuration example of an optical-image pickup apparatus that acquires an optical image of a subject with an SLO equipped with an adaptive optic system incorporating the present invention and a method for the same will be described with reference to FIG. 1.

This embodiment will be described when applied to an example in which aberration that occurs in the eye, which is the subject to be measured, is corrected by an adaptive optic system and an image of the fundus is acquired.

Figure 1:
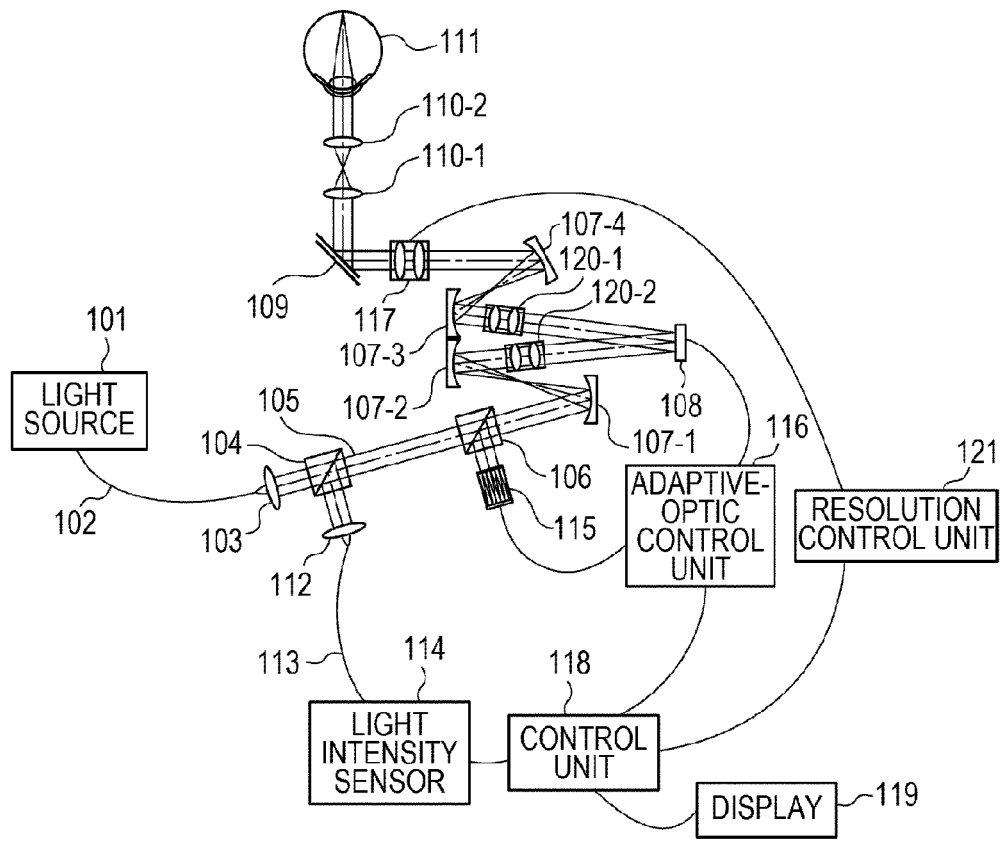
FIG. 1 is a schematic diagram of a configuration example of an optical-image pickup apparatus using an SLO equipped with an adaptive optic system according to a first embodiment of the present invention.

In FIG. 1, reference numeral 101 denotes a light source, which is a super luminescent diode (SLD) light source having a wavelength of 840 nm.

The wavelength of the light source 101 is not particularly limited; a wavelength of about 800 to 1,500 nm is suitably used for acquiring an image of the fundus to reduce the brightness of the subject and maintain the resolution.

Although this embodiment uses the SLD light source, a laser etc. may be used. Although this embodiment shares the light source for acquiring an image of the fundus and for measuring the wavefront, different light sources may be used individually, and the light beams may be multiplexed during the operation.

Light emitted from the light source 101 passes through a single-mode optical fiber 102 and is radiated as parallel measurement light 105 through a collimator 103.

The radiated measurement light 105 passes through a light splitting unit 104, which is a beam splitter, and is guided to an adaptive optic system.

The adaptive optic system is constituted by a light splitting unit 106, a wavefront sensor (in this embodiment, corresponding to an aberration measuring unit) 115, a wavefront correction device (in this embodiment, corresponding to a wavefront correction unit) 108, and reflecting mirrors 107-1 to 107-4 for guiding the measurement light 105 to the foregoing devices.

Here, the reflecting mirrors 107-1 to 107-4 are installed so that at least the pupil of the eye, the wavefront sensor 115, and the wavefront correction device 108 have optically conjugate relationship. This embodiment employs a beam splitter as the light splitting unit 106.

The adaptive optic system further includes effective-region setting units 120-1 and 120-2 for changing the effective region of the wavefront correction device 108.

The measurement light 105 is changed to a desired beam diameter through the effective-region setting unit 120-2 and is incident on the wavefront correction device 108.

The measurement light 105 reflected by the wavefront correction device 108 is again changed in beam diameter by the effective-region setting unit 120-1 and exits to the reflecting mirror 107-3.

Likewise, light that has returned from the eye is also changed in beam diameter by the effective-region setting unit 120-1 and is incident on the wavefront correction device 108, is again changed in beam diameter by the effective-region setting unit 120-2, and exits to the reflecting mirror 107-2.

The effective-region setting units 120-1 and 120-2 can be changed in the scaling of the beam diameter and is connected to a resolution control unit 121 (not shown).

That is, the resolution control unit 121 has a configuration also serving as an effective-region control unit that controls the effective-region setting units 120 (in this embodiment, corresponding to an effective-region setting unit) to change also the effective region of the wavefront correction device 108.

This embodiment uses a liquid-crystal spatial-phase modulator as the wavefront correction device 108.

Figure 2A:
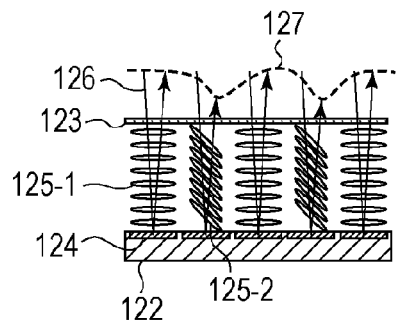
FIG. 2A is a schematic diagram of a reflective liquid-crystal optical modulator according to the first embodiment of the present invention.

FIG. 2A is a schematic diagram of a reflective liquid-crystal optical modulator.

This device has a configuration in which liquid crystal molecules 125 are sealed in a space between a base 122 and a cover 123.

The base 122 includes a plurality of pixel electrodes 124. The cover 123 includes a transparent counter electrode (not shown).

When no voltage is applied between the electrodes, the liquid crystal molecules 125 have an orientation denoted by

125-1. When a voltage is applied, the liquid crystal molecules 125 shift to an orientation denoted by 125-2, so that the refractive index to incident light changes.

By controlling the voltage to the pixel electrodes to change the refractive indices of the individual pixels, spatial phase modulation can be achieved. For example, in the case where incident light 126 is incident on the device, the light 126 that passes through the liquid crystal molecules 125-2 lags in phase behind the light 126 that passes through the liquid crystal molecules 125-1, resulting in forming a wavefront 127 shown in the drawing.

In general, the reflective liquid-crystal optical modulator is constituted by tens of thousands to hundreds of thousands of pixels.

Since a liquid crystal device has a polarization property, a polarizing device for adjusting the polarization of incident light is sometimes provided.

Another example of the wavefront correction device 108 is a deformable mirror. The deformable mirror can locally change the reflecting direction of light, for which various types of mirror are in practical use.

Figure 2B:
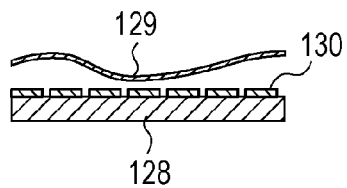
FIG. 2B is a schematic diagram for explaining a deformable mirror serving as a wavefront correction device according to the first embodiment.

FIG. 2B illustrates the cross section of an example of the device.

The device is constituted by a deformable film-like mirror surface 129 that reflects incident light, a base 128, actuators 130 disposed therebetween, and a supporting unit (not shown) that supports the mirror surface 129 from the periphery.

Examples of the operating principle of the actuators 130 include static electricity, a magnetic force, and a piezoelectric effect. The configuration of the actuators 130 depends on the operating principle.

The actuators 130 are arrayed in two dimensions on the base 128. The mirror surface 129 can be freely deformed by selectively driving the actuators 130. In general, the deformable mirror has tens to hundreds of actuators.

The light that has passed through the adaptive optic system is incident on a resolution setting unit 117. The resolution setting unit 117 changes the image acquisition resolution by changing the beam diameter of incident light and emits it.

Changing the beam diameter in a range from about 7 mm to 1 mm allows an image acquisition resolution from about 3 micrometers to 20 micrometers on the fundus.

The resolution setting unit 117 is controlled by the resolution control unit 121. The resolution control unit 121 operates in cooperation with a control unit 118.

A suitable example of the configuration of the resolution setting unit 117 is a configuration including a plurality of lenses whose positional relationship is adjusted so that the resolution can be changed continuously or discretely.

The measurement light 105 that has exited from the resolution setting unit 117 is scanned in one dimension or two dimensions by a scanning optical system 109.

This embodiment employs two galvanometer scanners as the scanning optical system 109, for main scanning (in the horizontal direction of the fundus) and for subscanning (in the vertical direction of the fundus). For higher-speed image acquisition, a resonant scanner is sometimes used as the main scanning of the scanning optical system 109.

To bring the scanners in the scanning optical system 109 into an optically conjugate state, optical devices, such as a mirror and a lens, may be disposed between the scanners.

The measurement light 105 scanned by the scanning optical system 109 is radiated to the eye 111 through eyepieces 110-1 and 110-2.

The measurement light 105 radiated to the eye 111 is reflected or scattered by the fundus.

Adjusting the positions of the eyepieces 110-1 and 110-2 allows optimum radiation depending on the visibility of the eye 111.

While lenses are used here as the eyepieces, spherical mirrors etc. may be used.

The light reflected and scattered by the retina of the eye 111 (feedback light) travels backward in the same path as that at the incidence and is partly reflected to the wavefront sensor 115 by the light splitting unit 106, in which the light is used to measure the wavefront thereof.

Figure 2C:
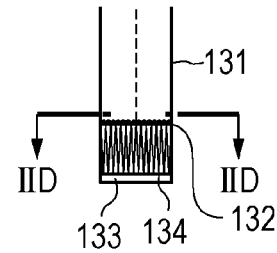
FIG. 2C is a schematic diagram illustrating the configuration of a Shack-Hartmann sensor serving as a wavefront sensor according to the first embodiment of the present invention.
Figure 2D:
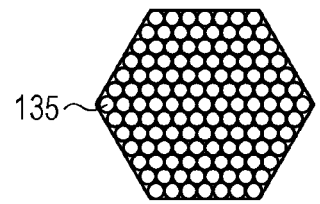
FIG. 2D is a schematic diagram illustrating the configuration of the Shack-Hartmann sensor.

This embodiment uses a Shack-Hartmann sensor as the wavefront sensor 115. FIGS. 2C and 2D show schematic diagrams of the Shack-Hartmann sensor. Reference numeral 131 denotes light whose wavefront is to be measured. The light 131 is collected on a focal plane 134 on a CCD sensor 133 through a microlens array 132.

FIG. 2D shows a state as viewed from a line IID-IID in FIG. 2C, which illustrates a state in which the microlens array 132 is constituted by a plurality of microlenses 135.

Since the light 131 is collected on the CCD sensor 133 through the microlenses 135, the light 131 is split into spots corresponding to the number of microlenses 135.

Figure 2E:
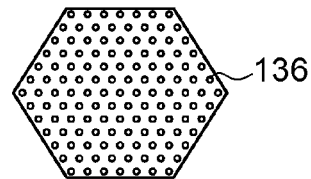
FIG. 2E is a schematic diagram illustrating a state in which wavefront measurement light is collected on a CCD sensor.

FIG. 2E shows a state in which the light 131 is collected on the CCD sensor 133. The light 131 that has passed through the microlenses 135 is collected on the spots 136.

Figure 2F:
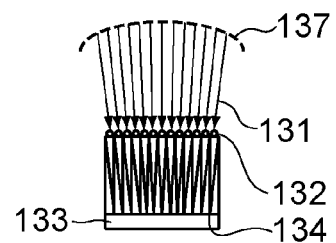
FIG. 2F is a schematic diagram in the case where a wavefront having a spherical aberration is measured.
Figure 2G:
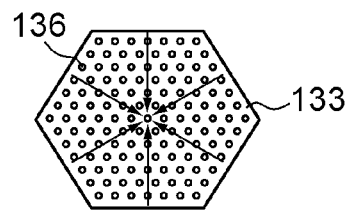
FIG. 2G is a schematic diagram in the case where a wavefront having a spherical aberration is measured.

The wavefront of the incident light 131 is calculated from the positions of the spots 136. For example, FIGS. 2F and 2G show schematic diagrams in the case where a wavefront having a spherical aberration is measured. The light 131 has a wavefront as indicated by reference numeral 137. The light 131 is collected on positions in locally perpendicular directions of the wavefront by the microlens array 132.

The collecting state of the CCD sensor 133 in this case is shown in FIG. 2G.

Since the light 131 has a spherical aberration, the spots 136 are concentrated in the center. By calculating the positions, the wavefront of the light 131 can be determined.

Although this embodiment employs the Shack-Hartmann sensor as the wavefront sensor 115, the wavefront sensor 115 is not limited thereto; another wavefront measuring unit, such as a curvature sensor, may be used, or a method of reversely calculating the wavefront from formed point images may be employed.

The reflected and scattered light that has passed through the light splitting unit 106 is partly reflected by the light splitting unit 104 and is guided to a light intensity sensor 114 through a collimator 112 and an optical fiber 113.

The light is converted to an electrical signal by the light intensity sensor 114, is formed into a fundus image by the control unit 118, and is displayed on a display 119.

The wavefront sensor 115 is connected to an adaptive-optics control unit 116 and transmits the wavefront of the received light to the adaptive-optics control unit 116.

The wavefront correction device 108 is also connected to the adaptive-optics control unit 116 and performs modulation indicated by the adaptive-optics control unit 116.

The adaptive-optics control unit 116 calculates the amount of modulation (correction amount) so as to correct the wavefront to a wavefront free from aberration on the basis the wavefront obtained from the measurement of the wavefront sensor 115 and instructs the wavefront correction device 108, thereby performing modulation according to the calculation result.

The measurement of the wavefront and the instruction to the wavefront correction device 108 are repeated, thus performing feedback control so as to provide an optimum wavefront.

This embodiment employs a 600-by 600-pixel reflective liquid-crystal spatial-phase modulator as the wavefront correction device 108.

In the case where a high resolution is set by the resolution setting unit 117, the wavefront correction device 108 is controlled such that the effective region of the wavefront correction device 108 is set to the whole region thereof by the effective-region setting units 120, and the modulation amounts of all the 600*600 pixels are calculated.

In contrast, in the case where a low resolution is set by the resolution setting unit 117, the wavefront correction device 108 is controlled such that the effective region of the wavefront correction device 108 is changed to a smaller region by the effective-region setting unit 120, and only the modulation amounts of a small number of pixels in the effective region are calculated.

An example of the correlation among the image acquisition resolution, the beam diameter, the effective region of the wavefront correction device 108, and the number of pixels used is shown in Table 1.

TABLE 1

| Image acquisition resolution | Beam diameter on pupil | Effective region of correction device | Number of pixels used |
|---|---|---|---|
| 3 micrometers | 7 mm | 12 mm | 360,000 |
| 5 micrometers | 4 mm | 8 mm | 160,000 |
| 20 micrometers | 1 mm | 4 mm | 40,000 |

Thus, by changing the effective region of the correction device depending on the image acquisition resolution to change the number of pixels used, a calculation load can be remarkably reduced. The proportion of calculation of correction amount in the total processing time is extremely high in the control of the correction device, so that the effect of reduction in processing time by changing the number of pixels is high.

According to inventor's calculation (the details are omitted), the total processing time is reduced to about one ninth by reducing the number of pixels from 600*600 to 200*200.

Next, a method for controlling the optical-image pickup apparatus of this embodiment will be described with reference to a flowchart in FIG. 3.

First, the control is started in step S101, and a resolution is set in step S102. Specifically, the resolution control unit 121 controls the resolution setting unit 117 to set the resolution by changing the beam diameter of the measurement light 105.

In step S103, the effective region of the wavefront correction device 108 is set by controlling the effective-region setting unit 120 in accordance with the resolution set in step S102.

Here, the effective region is set to a 12 mm square for a resolution of 3 micrometers, and an 8 mm square for a resolution of 5 micrometers, as shown on Table 1.

The basic flow of the adaptive optic system is as follows. In a state in which the measurement light 105 emitted from the light source 101 is radiated onto the eye 111, the aberration is measured by the wavefront sensor 115 in step S104.

In step S106, a correction amount is calculated by the adaptive-optics control unit 116 on the basis of the measurement, and in step S107, the wavefront correction device 108 is driven under the control of the adaptive-optics control unit 116. The above process is repeatedly performed.

Here, after the aberration is measured in step S104, it is determined in step S105 by the adaptive-optics control unit 116 whether the aberration falls below a preset reference value. The reference value may be either a value unique to the apparatus or a value set by the photographer.

In the case where the aberration exceeds the reference value, the processes from step S106 are executed.

In the case where the aberration falls below the reference value, the process moves to step S108, in which an image of the fundus is acquired, and it is determined in step S109 whether to terminate the image acquisition.

If a termination request has been given in step S109, the image acquisition is terminated in step S110. If no termination request is given, the process returns to step S104, in which the process of the adaptive optic system and the image acquisition are repeated.

The calculation of a correction amount in step S106 and the driving of the wavefront correction device 108 in step S107 are performed only for the region set by the effective-region setting unit 120.

The wavefront information measured in step S104 is fitted in a Zernike polynomial to calculate the wavefront in the form of the coefficients of the individual terms.

At the calculation of a correction amount in step S106, the correction amounts of the individual pixels are calculated using the calculated coefficients of the Zernike polynomial.

Here, if the image acquisition resolution is high, the accuracy cannot be achieved unless about Zernike high-order up to sixth-order is used for fitting; however, for low resolution, sufficient accuracy can be achieved even with, for example, Zernike low-order up to fourth-order.

Therefore, higher processing speed can be achieved by changing the order of Zernike depending on a set resolution.

Thus, this embodiment can suitably set the effective region of the wavefront correction device 108 depending on the resolution of image acquisition.

Furthermore, the aberration correction process can be speeded up by appropriately setting the number of effective pixels, thus allowing rapid high-quality image acquisition.

Second Embodiment

Figure 4:
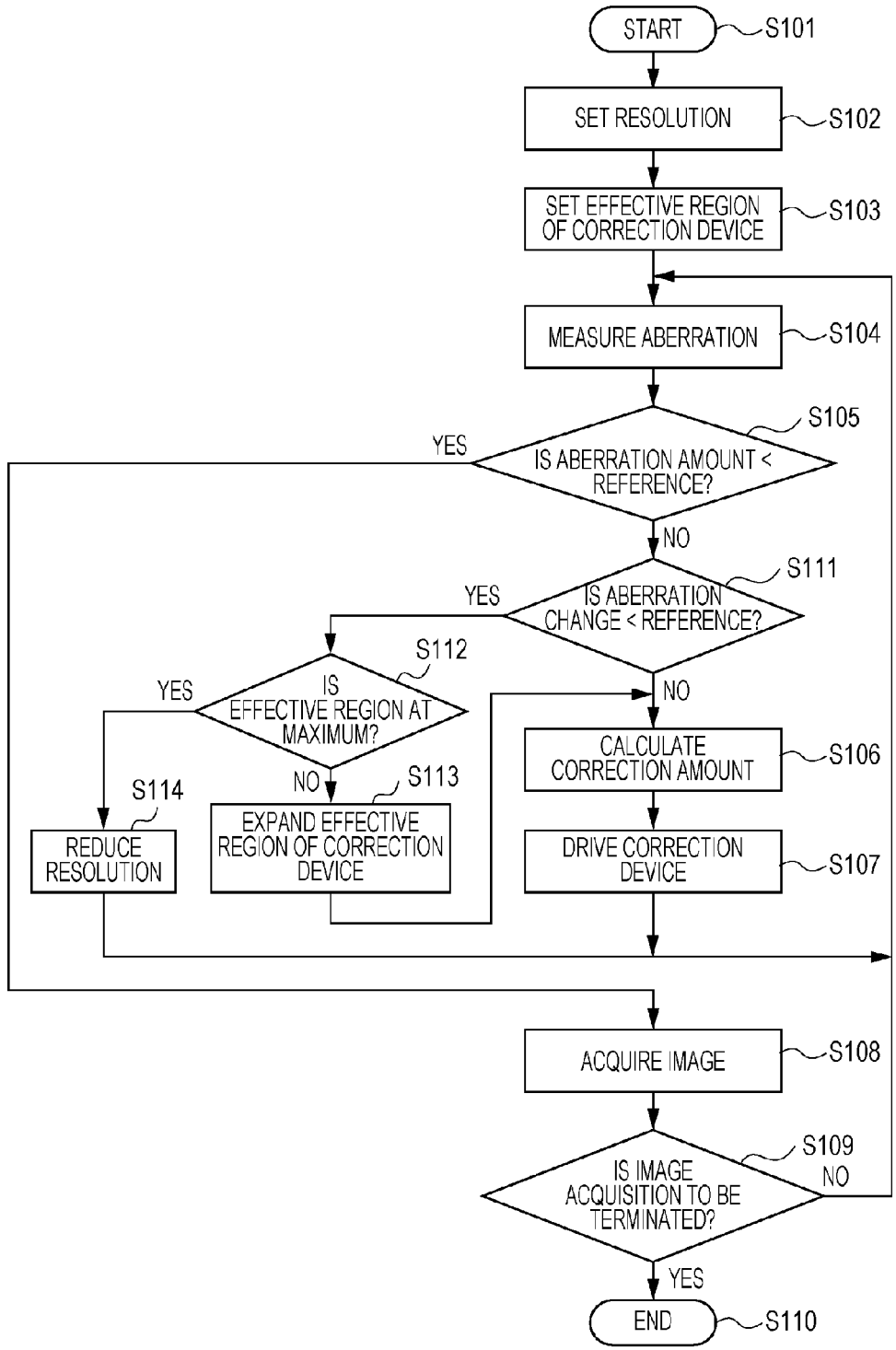
FIG. 4 is a flowchart of an example of the control step of an optical-image pickup apparatus according to a second embodiment of the present invention.

In a second embodiment, a configuration example of a method for controlling an optical-image pickup apparatus, different from the first embodiment, using an SLO equipped with an adaptive optic system incorporating the present invention will be described with reference to a flowchart in FIG. 4.

The basic configuration of this embodiment is the same as that of the first embodiment.

This embodiment is characterized in that the effective region is set depending on a set image acquisition resolution and an actual aberration amount.

First, the control is started in step S101, and a resolution is set in step S102. In step S103, the effective region of the wavefront correction device 108 is set by controlling the effective-region setting unit 120 in accordance with the resolution set in step S102. Here, the effective region is set to a 12 mm square for a resolution of 3 micrometers, and an 8 mm square for a resolution of 5 micrometers, as in the first embodiment.

The basic flow of the adaptive optic system is as follows. In a state in which the measurement light 105 emitted from the light source 101 is radiated onto the eye 111, the aberration is measured by the wavefront sensor 115 in step S104.

In step S106, a correction amount is calculated by the adaptive-optics control unit 116 on the basis of the measurement, and in step S107, the wavefront correction device 108 is driven under the control of the adaptive-optics control unit 116. The above process is repeatedly performed.

Here, after the aberration is measured in step S104, it is determined in step S105 by the adaptive-optics control unit 116 whether the aberration falls below a preset reference value. The reference value may be either a value unique to the apparatus or a value set by the photographer.

In the case where the aberration exceeds the reference value, the processes from step S106 are executed. In the case where the aberration falls below the reference value, the process moves to step S108, in which an image of the fundus is acquired, and it is determined in step S109 whether to terminate the image acquisition.

If a termination request has been given in step S109, the image acquisition is terminated in step S110. If no termination request is given, the process returns to step S104, in which the process of the adaptive optic system and the image acquisition are repeated.

Here, after step S105, the rate of change of aberration is determined in step S111. A high aberration change rate indicates that the process is halfway through the correction; a low aberration change rate and an aberration lower than the reference indicate that the correction capacity is insufficient.

Thus, if the aberration change rate is lower than the reference in step S111, the process moves to step S112, in which it is determined whether the effective region is at the maximum.

If the effective region is not at the maximum, the effective region is expanded in step S113 to enhance the correction capacity.

The amount of expansion may be either a predetermined proportion or a value obtained by calculating a necessary effective region from the measured aberration amount.

After the effective region is expanded in step S113, the process moves to step S106, in which a correction amount is calculated, and the wavefront correction device 108 is driven in step S107.

In the case where it is determined in step S112 that the effective region is at the maximum, the correction capacity of the correction device cannot be enhanced, and thus, the resolution is reduced in step S114. Decreasing the resolution reduces the aberration amount.

Thereafter, the process returns to step S104, in which the process of the adaptive optic system is performed.

Thus, this embodiment can suitably set the effective region of the wavefront correction device 108 depending on the resolution of image acquisition and the aberration amount of the subject to be measured.

Furthermore, the aberration correction process is speeded up by appropriately setting the number of effective pixels, thus allowing rapid high-quality image acquisition.

Third Embodiment

In a third embodiment, a configuration example of an optical-image pickup apparatus, different from the first embodiment, using an SLO equipped with an adaptive optic system incorporating the present invention will be described with reference to FIG. 5.

This embodiment is configured, unlike the first embodiment, to change image acquisition resolution and the effective regions of the wavefront sensor and the wavefront correction device.

Figure 5:
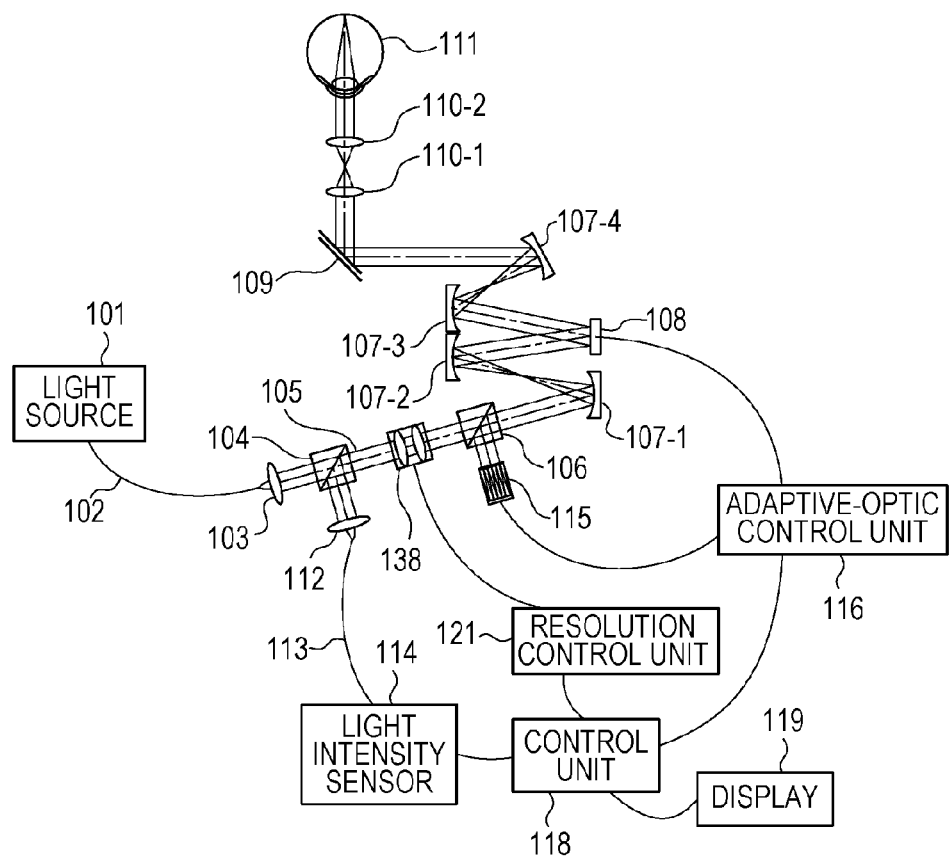
FIG. 5 is a schematic diagram of a configuration example of an optical-image pickup apparatus using an SLO equipped with an adaptive optic system according to a third embodiment of the present invention.

In FIG. 5, reference numeral 101 denotes a light source, which is an SLD light source having a wavelength of 840 nm.

Light emitted from the light source 101 passes through the single-mode optical fiber 102 and is radiated as parallel measurement light 105 through the collimator 103.

The radiated measurement light 105 passes through the light splitting unit 104 and is incident on a resolution and effective-region setting unit 138.

The resolution and effective-region setting unit 138 changes the image acquisition resolution and the effective regions of the wavefront sensor 115 and the wavefront correction device 108 by emitting the incident light 105, with its beam diameter changed.

The resolution and effective-region setting unit 138 is controlled by the resolution control unit 121.

Here, the light splitting unit 104 may be a beam splitter or the like, and the resolution and effective-region setting unit 138 may be a plurality of lenses whose positional relationship can be adjusted.

The measurement light 105 that has passed through the resolution and effective-region setting unit 138 is guided to the adaptive optic system. Although the adaptive optic system has the same configuration as that of the first embodiment, the effective-region setting units 120 for the wavefront correction device 108 are not provided in the adaptive optic system because the resolution and effective-region setting unit 138 serves also as an effective-region setting unit.

This embodiment also employs a liquid-crystal spatial-phase modulator as the wavefront correction device 108.

The measurement light 105 that has passed through the adaptive optic system is scanned in one dimension or two dimensions by the scanning optical system 109.

The measurement light 105 scanned by the scanning optical system 109 is radiated onto the eye 111 through the eyepieces 110-1 and 110-2.

The measurement light 105 radiated onto the eye 111 is reflected or scattered by the fundus.

Adjusting the positions of the eyepieces 110-1 and 110-2 allows optimum radiation depending on the visibility of the eye 111.

While lenses are used here as the eyepieces, spherical mirrors etc. may be used.

The light reflected and scattered by the retina of the eye 111 travels backward in the same path as that at the incidence and is partly reflected to the wavefront sensor 115 by the light splitting unit 106, in which the light is used to measure the wavefront thereof.

The reflected and scattered light that has passed through the light splitting unit 106 is partly reflected by the light splitting unit 104 and is guided to the light intensity sensor 114 through the collimator 112 and the optical fiber 113.

The light is converted to an electrical signal by the light intensity sensor 114, is formed into a fundus image by the control unit 118, and is displayed on the display 119.

The wavefront sensor 115 is connected to the adaptive-optics control unit 116 and transmits the wavefront of the received light to the adaptive-optics control unit 116.

The wavefront correction device 108 is also connected to the adaptive-optics control unit 116 and performs modulation indicated by the adaptive-optics control unit 116.

The adaptive-optics control unit 116 calculates the amount of modulation to correct the wavefront to a wavefront free from aberration on the basis of the wavefront obtained from the wavefront sensor 115 and instructs the wavefront correction device 108 to perform modulation according to the calculation result.

The measurement of the wavefront and the instruction to the wavefront correction device 108 are repeated, thus performing feedback control so as to provide an optimum wavefront.

This embodiment employs a 600-by 600-pixel reflective liquid-crystal spatial-phase modulator as the wavefront correction device 108.

In the case where a high resolution is set by the resolution and effective-region setting unit 138, the wavefront correction device 108 is controlled such that the effective region of the wavefront correction device 108 is set to the whole region thereof, and the modulation amounts of all the 600*600 pixels are calculated.

In contrast, in the case where a low resolution is set by the resolution and effective-region setting unit 138, the wavefront correction device 108 is controlled such that the effective region of the wavefront correction device 108 is changed to a small region, and only the modulation amounts of a small number of pixels in the effective region are calculated. As for the wavefront correction device 108, the effective region of the wavefront sensor 115 is changed depending on the setting of the resolution and effective-region setting unit (in this embodiment, corresponding to an aberration measuring and effective-region setting unit) 138.

An example of the correlation among image acquisition resolution, the beam diameter, the effective region of the wavefront sensor 115, the effective region of the wavefront correction device 108, and the number of pixels used is shown in Table 2.

TABLE 2

| Image acquisition resolution | Beam diameter on pupil | Effective region of wavefront sensor | Effective region of correction device | Number of pixels used |
|---|---|---|---|---|
| 3.5 micrometers | 6 mm | 8 mm | 12 mm | 360,000 |
| 5 micrometers | 4 mm | 5.4 mm | 8 mm | 160,000 |
| 20 micrometers | 1 mm | 1.5 mm | 2 mm | 10,000 |

Unlike the first embodiment, since both the resolution and the effective region are changed by the resolution and effective-region setting unit 138, the proportions of changes thereof are the same although the area of the effective region of the wavefront correction device 108 and the area of the region in which the aberration is to be measured differ.

Thus, by changing the effective regions of the wavefront sensor 115 and the wavefront correction device 108 depending on the image acquisition resolution, the number of pixels used is changed.

Also in this embodiment, the effective region of the wavefront correction device 108 can be suitably set depending on the image acquisition resolution by performing the same process as in the first embodiment or the second embodiment.

Furthermore, the aberration correction process can be speeded up by appropriately setting the number of effective pixels, thus allowing rapid high-quality image acquisition.

Furthermore, the resolution setting unit and the effective-region setting unit can be combined.

Fourth Embodiment

Figure 6:
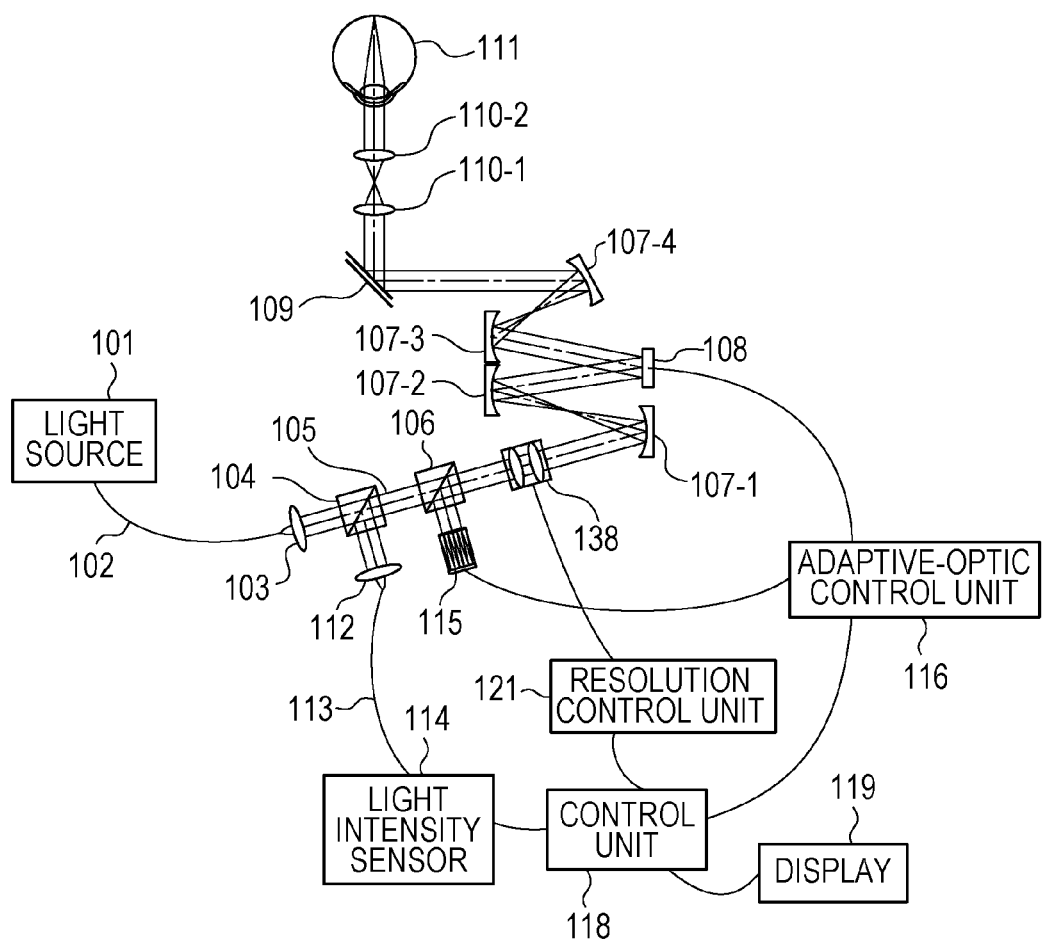
FIG. 6 is schematic diagram of a configuration example of an optical-image pickup apparatus using an SLO equipped with an adaptive optic system according to a fourth embodiment of the present invention.

In a fourth embodiment, a configuration example of an optical-image pickup apparatus, different from the third embodiment, using an SLO equipped with an adaptive optic system incorporating the present invention will be described as a third embodiment with reference to FIG. 6.

This embodiment is configured, unlike the third embodiment, to change image acquisition resolution and the effective region of the wavefront sensor.

That is, this embodiment is similar to the third embodiment except that the resolution and effective-region setting unit 138 is adjacent to the wavefront correction device 108 with respect to the light splitting unit 106 connected to the wavefront sensor 115.

The resolution and effective-region setting unit 138 changes the image acquisition resolution and the effective region of the wavefront correction device 108 by emitting the incident light 105, with its beam diameter changed, but does not change the effective region of the wavefront sensor 115.

The number of microlenses of the Shack-Hartmann sensor that is the wavefront sensor 115 is not so large as compared with the spatial-phase modulator that is the wavefront correction device 108.

Therefore, this configuration is sometimes adopted by placing more importance on the accuracy of wavefront measurement than enhancement of calculation speed by reducing the effective region.

An example of the correlation among the image acquisition resolution, the beam diameter, the effective region of the wavefront sensor 115, the effective region of the wavefront correction device 108, and the number of pixels used is shown in Table 3.

TABLE 3

| Image acquisition resolution | Beam diameter on pupil | Effective region of wavefront sensor | Effective region of correction device | Number of pixels used |
|---|---|---|---|---|
| 3.5 micrometers | 6 mm | 8 mm | 12 mm | 360,000 |
| 5 micrometers | 4 mm | 8 mm | 8 mm | 160,000 |
| 20 micrometers | 1 mm | 8 mm | 2 mm | 10,000 |

Unlike the third embodiment, the effective region of the wavefront sensor 115 is not changed even if the resolution is changed. Thus, by changing the effective region of the wavefront correction device 108 depending on the image acquisition resolution, the number of pixels used is changed.

Also in this embodiment, the number of effective pixels of the wavefront correction device 108 can be suitably set depending on the image acquisition resolution by performing the same process as in the first embodiment or the second embodiment.

Furthermore, the aberration correction process can be speeded up by appropriately setting the number of effective pixels, thus allowing rapid high-quality image acquisition.

Furthermore, the resolution setting unit and the effective-region setting unit can be combined without decreasing the accuracy of wavefront measurement.

Fifth Embodiment

In a fifth embodiment, a configuration example of an optical-image pickup apparatus using an OCT system equipped with an adaptive optic system incorporating the present invention will be described with reference to FIG. 7.

Figure 7:
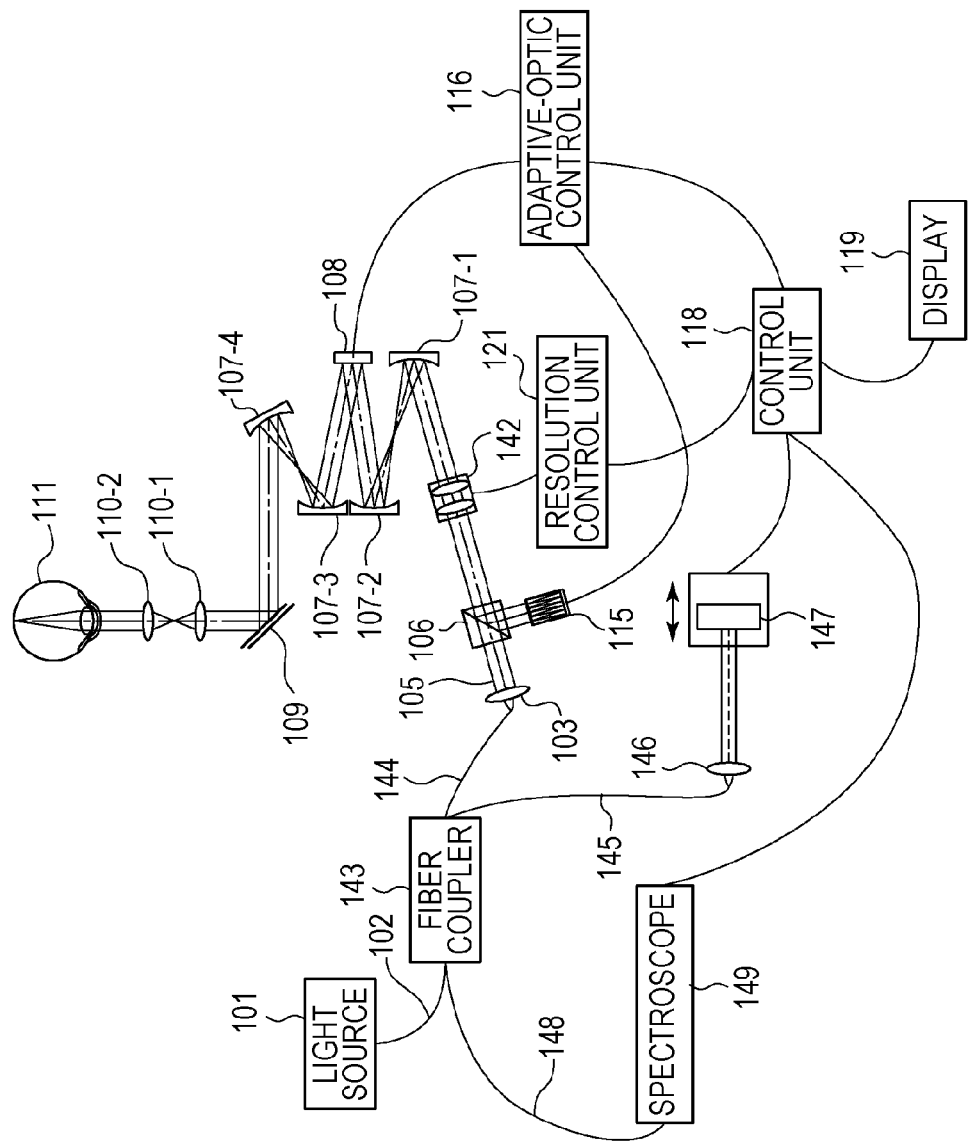
FIG. 7 is a schematic diagram of a configuration example of an optical-image pickup apparatus using an OCT system equipped with an adaptive optic system according to a fifth embodiment of the present invention.

In FIG. 7, reference numeral 101 denotes a light source, which is in this embodiment an SLD light source having a wavelength of 840 nm.

The light source 101 should have low coherence, as which an SLD light source having a wavelength of 30 nm or more is suitably used. Furthermore, an ultrashort pulse laser, such as a titanium-sapphire laser, can be used as the light source.

Light emitted from the light source 101 passes through the single-mode optical fiber 102 and is guided to a fiber coupler 143.

The light is split into a measurement light path 144 and a reference light path 145 by the fiber coupler 143. The fiber coupler 143 has a split ratio of 10 to 90 so that 10% of the input light quantity is introduced to the measurement light path 144.

The light that has passed through the measurement light path 144 becomes parallel measurement light through the collimator 103.

The configuration following the collimator 103 is the same as that of the fourth embodiment, in which the light is radiated onto the eye 111 through the adaptive optic system and the scanning optical system, and the light reflected and scattered by the eye 111 travels again through the same path to reach the fiber coupler 143 by the guide of the optical fiber 144.

On the other hand, reference light that has passed through the reference light path 145 exits from a collimator 146 and is reflected by an optical-path-length varying portion 147 to return to the fiber coupler 143.

The measurement light and the reference light that have reached the fiber coupler 143 are multiplexed and are guided to a spectroscope 149 through an optical fiber 148.

A tomogram of the fundus is formed by the control unit 118 on the basis of coherent light information acquired by the spectroscope 149. The control unit 118 can acquire an image at a desired depth by controlling the optical-path-length varying portion 147.

The wavefront is measured by the wavefront sensor 115, and the wavefront correction device 108 is driven to cancel the wavefront aberration, as in the first embodiment.

Furthermore, setting of the resolution and changing of the effective region of the wavefront correction device 108 are performed, as in the fourth embodiment. Thus, since the effective region of the wavefront correction device 108 is suitably set depending on the resolution of image acquisition also in this embodiment, the aberration correction process is speeded up, thus allowing rapid image acquisition.

The OCT can provide a tomogram; however, if the resolution is improved by increasing the NA for incident light, the depth of field becomes shallow, thus forming an in-focus portion and a defocus portion in one tomogram.

Thus, it is also possible to adopt a method of acquiring an image by dividing a depthwise image capture region to a width corresponding to about the depth of field and thereafter combining images with the individual depths to acquire a tomogram in which focus is achieved in the whole region.

Figure 3:
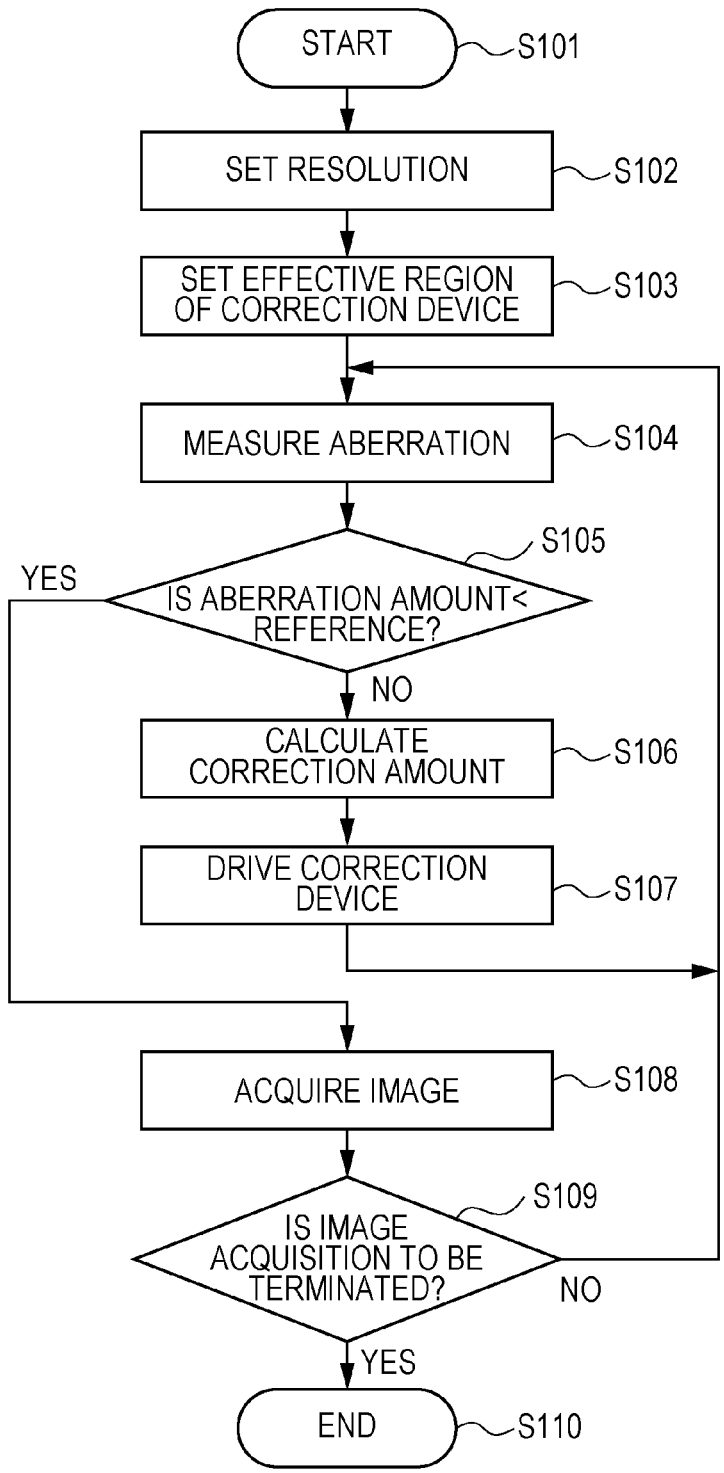
FIG. 3 is a flowchart of an example of the control step of the optical-image pickup apparatus according to the first embodiment of the present invention.

In this case, by changing a depthwise region in which an image is acquired by one image acquisition depending on the resolution changed in step S102 of FIG. 3, an image having a wide in-focus region can be acquired quickly and easily.

Also in this embodiment, the number of effective pixels of the wavefront correction device 108 can be suitably set depending on the image acquisition resolution.

Furthermore, the aberration correction process can be speeded up by appropriately setting the number of effective pixels, thus allowing rapid high-quality image acquisition.

Furthermore, the resolution setting unit and the effective-region setting unit can be combined without decreasing the accuracy of wavefront measurement.

Sixth Embodiment

In a sixth embodiment, a configuration example of an optical-image pickup apparatus that acquires an optical image of a subject using an SLO equipped with an adaptive optic system incorporating the present invention and a method for the same will be described with reference to FIG. 8. This embodiment will be described when applied to an example in which aberration that occurs in the eye, which is the subject to be measured, is corrected by an adaptive optic system and an image of the fundus is acquired.

Figure 8:
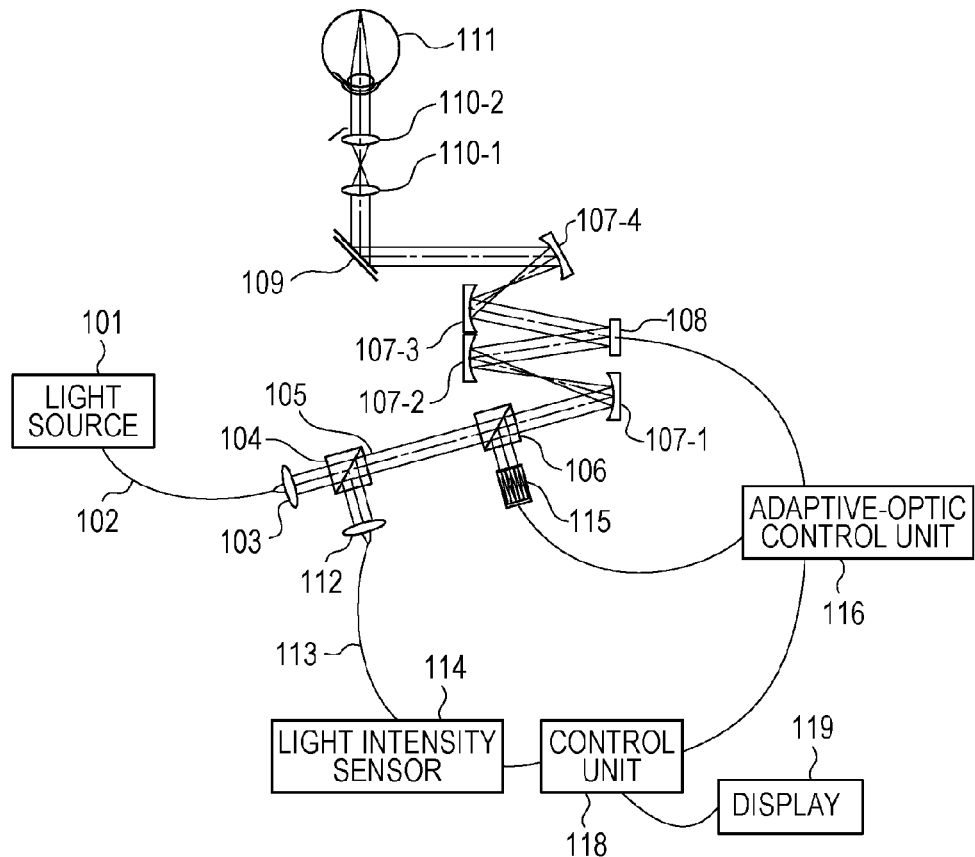
FIG. 8 is a schematic diagram of a configuration example of an optical-image pickup apparatus using an SLO equipped with an adaptive optic system according to a sixth embodiment of the present invention.

In FIG. 8, reference numeral 101 denotes a light source, which is a super luminescent diode (SLD) light source having a wavelength of 840 nm.

The wavelength of the light source 101 is not particularly limited; a wavelength of about 800 to 1,500 nm is suitably used for acquiring an image of the fundus to reduce the brightness of the subject and maintain the resolution.

Although this embodiment uses the SLD light source, a laser etc. may be used. Although this embodiment shares the light source for acquiring an image of the fundus and for measuring the wavefront, different light sources may be used individually, and the light beams may be multiplexed during the operation.

Light emitted from the light source 101 passes through the single-mode optical fiber 102 and is radiated as parallel measurement light 105 through the collimator 103.

The radiated measurement light 105 passes through the light splitting unit 104, which is a beam splitter, and is guided to the adaptive optic system.

The adaptive optic system is constituted by the light splitting unit 106, the wavefront sensor (in this embodiment, corresponding to an aberration measuring unit) 115, the wavefront correction device (in this embodiment, corresponding to a wavefront correction unit) 108, and the reflecting mirrors 107-1 to 107-4 for guiding the measurement light 105 to the foregoing devices.

Here, the reflecting mirrors 107-1 to 107-4 are installed so that at least the pupil of the eye, the wavefront sensor 115, and the wavefront correction device 108 have optically conjugate relationship. This embodiment employs a beam splitter as the light splitting unit 106.

The measurement light 105 is incident on the wavefront correction device 108, at which the measurement light 105 is reflected and exits to the reflecting mirror 107-3.

Figure 9A:
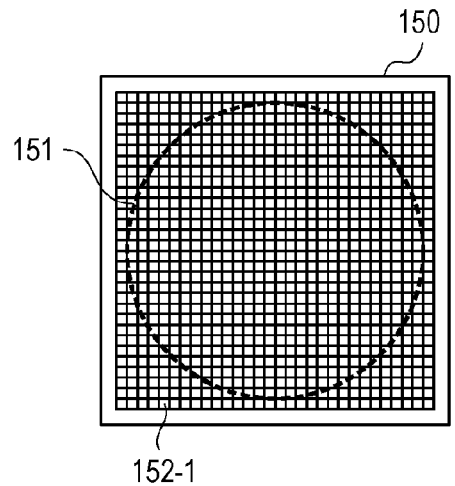
FIG. 9A is a schematic diagram of a spatial-phase modulator according to the sixth embodiment of the present invention.
Figure 9B:
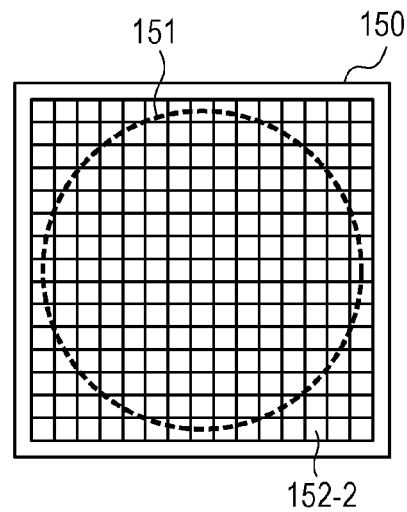
FIG. 9B is a schematic diagram of the spatial-phase modulator according to the sixth embodiment of the present invention.
Figure 9C:
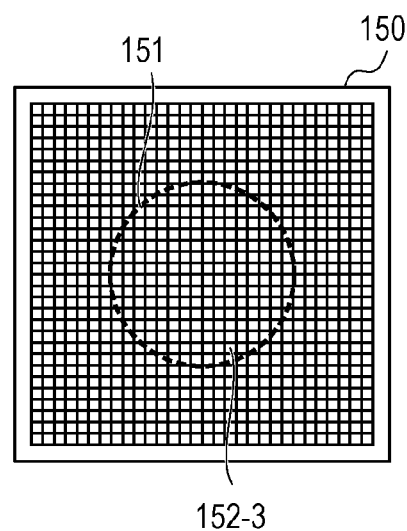
FIG. 9C is a schematic diagram of the spatial-phase modulator according to the sixth embodiment of the present invention.

The embodiment uses a liquid-crystal spatial-phase modulator as the wavefront correction device 108. Although the basic configuration of the spatial-phase modulator is the same as that described in the first embodiment, the resolution of the effective region used for modulation can be changed. FIGS. 9A to 9C illustrate the configurations of pixels of the spatial-phase modulator used in this embodiment. Reference numeral 150 denotes the pixel surface of the wavefront correction device 108, which includes 30*30 pixels 152. A region irradiated with the measurement light 105 is indicated by a circle 151. FIG. 9A illustrates a pixel configuration in the case where all pixels 152-1 are individually modulated. Individually modulating the pixels 152-1 allows accurate control of even a complicated waveform. However, a significant calculation load is imposed on this configuration because it is necessary to calculate the individual modulation amounts of the pixels 152-1 at a 30-by 30-pixel resolution.

FIG. 9B illustrates a case in which pixel sets 152-2 each including four pixels (2*2 pixels) are modulated at a 15-by 15-pixel resolution. A total of 225 pixel sets 152-2 are modulated for wavefront control, which is substantially sufficient number of pixels to correct low-order aberrations which occupy most of aberrations of the eye, such as defocus, astigmatism, and spherical aberration. Since calculation of modulation amount is made for each pixel set, that is, merely 225 pixel sets, which remarkably reduces a calculation load. The pixel set 152-2 is not limited to 2*2 pixels but may include more pixels. The larger the number of pixels in each pixel set, the smaller the calculation load becomes although the accuracy of wavefront control decreases. Thus, the resolution should be determined in consideration of necessary correction accuracy and the calculation load.

It is also possible to configure to change the effective region of the wavefront correction device 108 by providing a beam-diameter varying optical system (not shown) ahead or behind the wavefront correction device 108. FIG. 9C illustrates the pixel configuration of the spatial-phase modulator in the case where the effective region is changed. The measurement light 105 irradiates only the region indicated by the circle 151 of the pixel surface 150 of the spatial-phase modulator. Accordingly, wavefront control is performed for pixels 152-3 in this region and in the vicinity thereof. The example in FIG. 9C illustrates a case in which a region with a diameter of 16 pixels is irradiated, in which pixels to be controlled are the central 18*18 pixels, that is, 324 pixels in total. This number of pixels is also substantially sufficient to correct low-order aberrations which occupy most of aberrations of the eye, such as defocus, astigmatism, and spherical aberration. Calculation of the modulation amount is remarkably reduced as compared with a case in which the calculation is made for the whole region.

The measurement light 105 that has passed through the adaptive optic system is scanned in one dimension or two dimensions by the scanning optical system 109. The measurement light 105 scanned by the scanning optical system 109 is radiated to the eye 111 through the eyepieces 110-1 and 110-2.

The measurement light 105 radiated onto the eye 111 is reflected or scattered by the fundus.

The light reflected and scattered by the retina of the eye 111 travels backward in the same path as that at the incidence and is partly reflected to the wavefront sensor 115 by the light splitting unit 106, in which the light is used to measure the wavefront thereof.

Although this embodiment uses a Shack-Hartmann sensor as the wavefront sensor 115, it is not limited thereto; another wavefront measuring unit, such as a curvature sensor, may be used, or a method of reversely calculating the wavefront from formed point images may be employed.

The reflected and scattered light that has passed through the light splitting unit 106 is partly reflected by the light splitting unit 104 and is guided to the light intensity sensor 114 through the collimator 112 and the optical fiber 113.

The light is converted to an electrical signal by the light intensity sensor 114, is formed into a fundus image by the control unit 118, and is displayed on the display 119.

The wavefront sensor 115 is connected to the adaptive-optics control unit 116 and transmits the wavefront of the received light to the adaptive-optics control unit 116.

The wavefront correction device 108 is also connected to the adaptive-optics control unit 116 and performs modulation indicated by the adaptive-optics control unit 116.

The adaptive-optics control unit 116 calculates the amount of modulation (correction amount) to correct the wavefront to a wavefront free from aberration on the basis of the wavefront obtained from the measurement on the wavefront sensor 115 and instructs the wavefront correction device 108 to perform modulation according to the calculation result.

The measurement of the wavefront and the instruction to the wavefront correction device 108 are repeated, and thus a feedback control is performed to provide an optimum wavefront.

In this embodiment, as described above, the resolution of the spatial-phase modulator that is the wavefront correction device 108 can be freely designated. The resolution is changed (reset) depending on the state of feedback control for wavefront correction.

Figure 10:
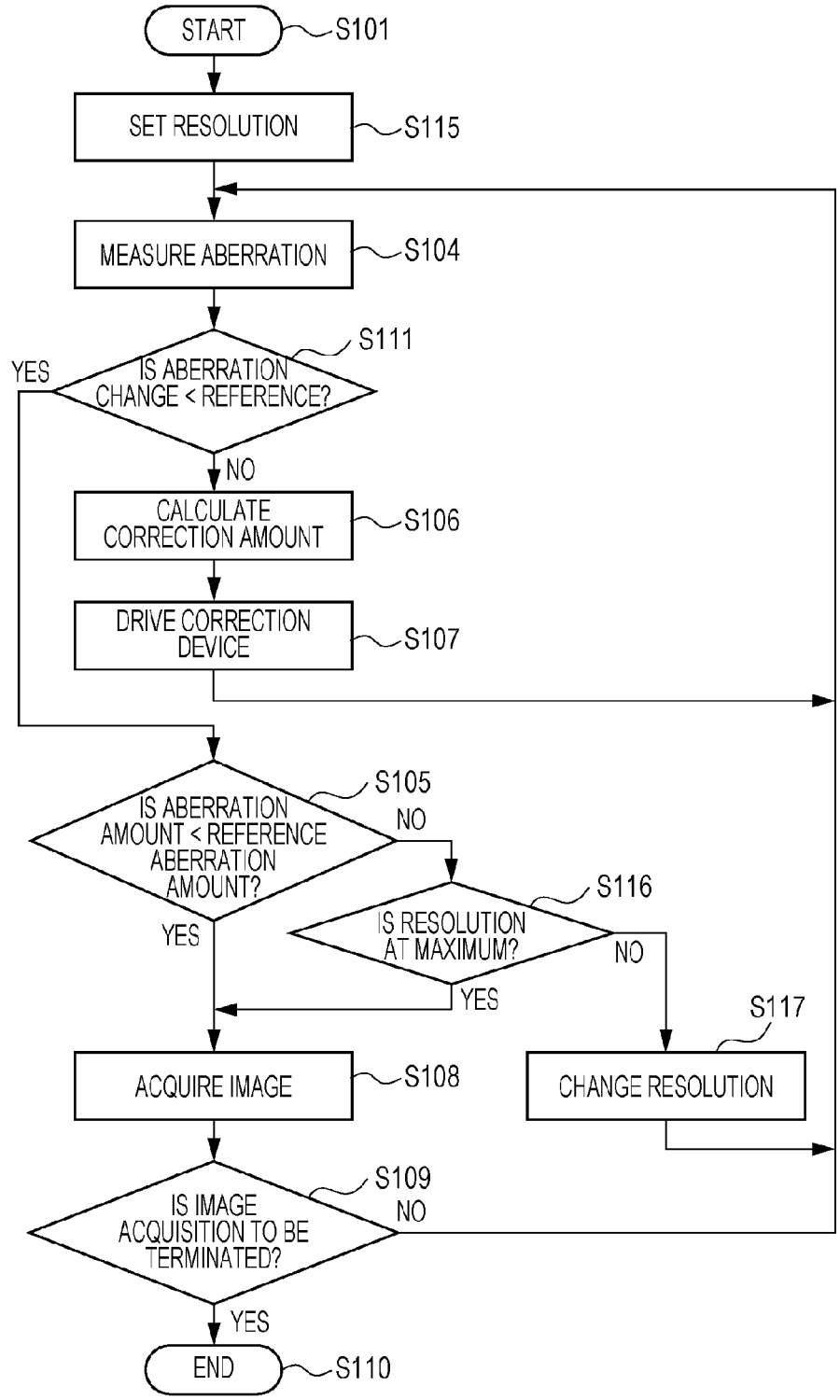
FIG. 10 is a flowchart of an example of the control step of the optical-image pickup apparatus according to the sixth embodiment of the present invention.

Next, a method for controlling the optical-image pickup apparatus of this embodiment will be described with reference to a flowchart in FIG. 10.

First, the control is started in step S101, and the resolution of the spatial-phase modulator is set in step S115. The resolution is set to 15*15 pixels. As described above, the effective region of the spatial-phase modulator may be set to a narrow region not by changing the resolution but by changing the beam diameter, as described above.

The basic flow of the adaptive optic system is as follows. In a state in which the measurement light 105 emitted from the light source 101 is radiated onto the eye 111, the aberration is measured by the wavefront sensor 115 in step S104.

In step S106, a correction amount is calculated by the adaptive-optics control unit 116 at the resolution set in step S115 on the basis of the measurement, and in step S107, the wavefront correction device 108 is driven under the control of the adaptive-optics control unit 116. The above process is repeatedly performed. Since the resolution is set low in step S115, the processing time in step S106 is short, so that the basic flow from step S104 to S107 is performed at very high speed.

Here, after the aberration is measured in step S104, it is determined in step S111 by the adaptive-optics control unit 116 whether the aberration change falls below a preset reference value. The reference value may be either a value unique to the apparatus or a value set by the photographer.

In the case where the aberration change exceeds the reference value, the processes following step S106 are executed.

In the case where the aberration change falls below the reference value, the process moves to step S105, in which it is determined whether the aberration amount falls below the reference of the aberration amount.

In the case where the aberration amount falls below the reference value, the process moves to step S108, in which an image of the fundus is acquired, and it is determined in step S109 whether to terminate the image acquisition.

If a termination request has been given in step S109, the image acquisition is terminated in step S110. If no termination request is given, the process returns to step S104, in which the process of the adaptive optic system and the image acquisition are repeated.

In the case where the aberration amount exceeds the reference value in step S105, the process moves to step S116, in which it is determined whether the set resolution is the maximum resolution of the wavefront correction device 108. If the set resolution is not the maximum resolution, the process moves to step S117, in which the resolution is set to a resolution higher than the current set resolution. Thereafter, the process moves to step S104, and the basic flow of the adaptive optics is repeated.

If it is determined in step S116 that the resolution is set at the maximum resolution, it is determined that it is the limit of the aberration collection capacity, and the process moves to step S108, in which image acquisition is performed.

Executing the aberration correction feedback loop at a low resolution at the start of the aberration correction, as in the foregoing flow, remarkably increases the processing speed as compared with feedback control at the maximum resolution, thereby reducing the time for reaching a state in which most of the aberration of the eye is corrected. If the aberration in this stage is in a state in which image acquisition is possible, image acquisition is immediately performed, thus remarkably reducing the time until the start of image acquisition. Even if the aberrations is not sufficiently corrected at this stage, the remaining aberration can be sufficiently corrected by several times of feedback because it is small high-order aberration, thus reducing the time until the start of image acquisition as compared with a case in which the apparatus is controlled at high resolution from the beginning.

In this embodiment, although a low resolution is set in step S115, it is also possible to measure the aberration before setting a resolution, and then set a suitable resolution. Furthermore, it is also possible to increase the feedback speed by adjusting the resolution to improve a flow-up performance to the state of tear and refraction adjustment after an aberration amount at which image acquisition can be performed is reached.

Thus, according to this embodiment, the wavefront correction device 108 can be controlled at suitable resolutions at the individual timings of the feedback, so that the aberration correction process can be speeded up, thus reducing the time until the start of image acquisition.

Furthermore, for the methods for controlling the optical-image pickup apparatuses of the embodiments described above, a program for a computer to execute the control methods can be produced, and the program may be stored in a storage medium so that the computer can read the program.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-262387, filed on Nov. 17, 2009, and Japanese Patent Application No. 2010-209319, filed on Sep. 17, 2010 which are hereby incorporated by reference herein in their entirety.

The invention claimed is:

1. A method for controlling an optical-image pickup apparatus configured to radiate measurement light onto a subject, to correct an aberration generated at the subject with a correction unit, and to acquire an optical image of the subject, the method comprising:
a changing step of changing a size of an effective region of the correction unit depending on a beam diameter of light to be incident on the correction unit;
a measuring step of measuring an aberration generated at the subject;
a calculating step of calculating a correction amount of the changed effective region so as to correct the aberration on the basis of the measured aberration; and
a control step of controlling the changed effective region of the correction unit on the basis of the calculated correction amount.

2. The method for controlling the optical-image pickup apparatus according to claim 1, wherein the method repeats the measuring step to the control step, and during the repeated process, the method further comprises a re-changing process of re-changing the size of the effective region.

3. The method for controlling the optical-image pickup apparatus according to claim 1, the method further comprising a resolution changing step of changing a resolution of the optical image when acquiring the optical image of the subject;
wherein the changing of the resolution in the resolution changing step is performed by changing the beam diameter of the measurement light.

4. The method for controlling the optical-image pickup apparatus according to claim 3, wherein the aberration is described by a Zernike polynomial, and the order of the Zernike polynomial is changed depending on the resolution.

5. The method for controlling the optical-image pickup apparatus according to claim 3, wherein the size of the effective region is changed depending on the changed resolution and the measured aberration.

6. The method for controlling the optical-image pickup apparatus according to claim 1, wherein at the changing the size of the effective region in the changing step, a size of a region for use in measuring the aberration is also changed.

7. The method for controlling the optical-image pickup apparatus according to claim 1, wherein the size of the effective region and the size of the region for use in measuring the aberration differ.

8. A non-transitory computer-readable medium encoded with instructions for a computer to execute the method for controlling the optical-image pickup apparatus according to claim 1.

9. The method according to claim 1, wherein the subject is an eye, and
wherein the correction unit is optically conjugate with an anterior ocular segment of the eye.

10. An optical-image pickup apparatus configured to radiate measurement light onto a subject, to correct an aberration generated at the subject with a correction unit, and to acquire an optical image of the subject, the apparatus comprising:
a changing unit configured to change a size of an effective region of the correction unit depending on a beam diameter of light to be incident on the correction unit;
an aberration measuring unit configured to measure an aberration generated at the subject;
a calculating unit configured to calculate a correction amount of the changed effective region so as to correct the aberration on the basis of the measured aberration; and
a control unit configured to control the changed effective region of the correction unit on the basis of the calculated correction amount.

11. The optical-image pickup apparatus according to claim 10, further comprising a resolution changing unit configured to change a resolution of the optical image when acquiring the optical image of the subject;
wherein the resolution changing unit includes a unit configured to change the beam diameter of the measurement light.

12. The optical-image pickup apparatus according to claim 10, further comprising an effective-region changing unit configured to change the effective region of the aberration measuring unit.

13. The optical-image pickup apparatus according to claim 10, wherein the correction unit includes a spatial-phase modulator.

14. The apparatus according to claim 10, wherein the subject is an eye, and wherein the correction unit is optically conjugate with an anterior ocular segment of the eye.

15. A method for controlling an optical-image pickup apparatus configured to radiate measurement light onto a subject, to correct an aberration generated at the subject with a correction unit, and to acquire an optical image of the subject, the method comprising:
a changing step of changing a size of an effective region of the correction unit based on a diameter of the measurement light reflected from the subject on the correction unit;
a measuring step of measuring an aberration generated at the subject; and a control step of controlling the changed effective region of the correction unit on the basis of the measured aberration.

16. A non-transitory computer-readable medium encoded with instructions for a computer to execute the method for controlling the optical-image pickup apparatus according to claim 15.

17. The method according to claim 15, wherein the subject is an eye, and wherein the correction unit is optically conjugate with an anterior ocular segment of the eye.

18. A method for controlling an optical-image pickup apparatus configured to radiate measurement light onto a subject, to correct an aberration generated at the subject with a correction unit, and to acquire an optical image of the subject, the method comprising:
　　a changing step of changing the number of pixel sets of an effective region at the correction unit based on a diameter of the measurement light, on the correction unit, reflected from the subject;
　　a measuring step of measuring an aberration generated at the subject; and
　　a control step of controlling the effective region of the correction unit on the basis of the measured aberration and the changed number of pixel sets.

19. A non-transitory computer-readable medium encoded with instructions for a computer to execute the method for controlling the optical-image pickup apparatus according to claim 18.

20. The method according to claim 18, wherein the subject is an eye, and wherein the correction unit is optically conjugate with an anterior ocular segment of the eye.

21. An optical-image pickup apparatus configured to radiate measurement light onto a subject, to correct an aberration generated at the subject with a correction unit, and to acquire an optical image of the subject, the apparatus comprising:
　　a changing unit configured to change the number of pixel sets of an effective region at the correction unit based on a diameter of the measurement light, on the correction unit, reflected from the subject;
　　an aberration measuring unit configured to measure an aberration generated at the subject; and
　　a control unit configured to control the effective region of the correction unit on the basis of the measured aberration and the changed number of pixel sets.

22. The apparatus according to claim 21, wherein the subject is an eye, and wherein the correction unit is optically conjugate with an anterior ocular segment of the eye.

* * * * *